United States Patent [19]

Schreiber et al.

[11] 4,105,759

[45] Aug. 8, 1978

[54] AMINE MONOFLUOROPHOSPHATES IN DENTIFRICES

[75] Inventors: Ronald Stanley Schreiber, Highland Park, N.J.; Edward John Duff, Sandbach, England

[73] Assignee: Colgate-Palmolive Company, New York, N.Y.

[21] Appl. No.: 782,114

[22] Filed: Mar. 28, 1977

[51] Int. Cl.² ............................ C07F 9/26; A61K 7/18
[52] U.S. Cl. .................................. 424/52; 260/543 F
[58] Field of Search ........................ 260/543 F, 543 P; 424/52

[56] References Cited

U.S. PATENT DOCUMENTS

| | | | |
|---|---|---|---|
| 2,489,917 | 11/1949 | McCombre et al. | 260/543 F |
| 2,678,334 | 5/1954 | Hartley et al. | 260/543 F |
| 4,011,310 | 3/1977 | Soldati et al. | 424/52 |

*Primary Examiner*—Norman Morgenstern
*Attorney, Agent, or Firm*—Robert L. Stone; Murray M. Grill; Herbert S. Sylvester

[57] ABSTRACT

Novel bis long chain ($C_8$–$C_{18}$) amine monofluorophosphates, particularly useful as substantive, slow release fluoride agents for anti-caries prophylaxis; the process of preparing said amine monofluorophosphates; and compositions containing an effective amount of said fluoride agent admixed with a pharmaceutical carrier, more particularly an oral composition.

9 Claims, No Drawings

AMINE MONOFLUOROPHOSPHATES IN DENTIFRICES

Dean and coworkers were the first to provide definite proof of the protective action of fluoride against dental decay, described in *Public Health Reporter* (*Wash.*), 48,703 (1933). The subsequent discovery that the fluoride ion at low levels reacts with calcium phosphates and with apatite in dental enamel initiated extensive efforts to develop effective means of incorporating fluoride ions into the enamel surface of teeth by topical applications. Many methods of application have been tested such as the topical application of concentrated solutions of sodium fluoride, sodium monofluorophosphate, calcium monofluorophosphate (British patent No. 1,270,752), stannous fluoride fluoride-orthophosphoric acid combinations, or amine fluorides; the application of fluoride gels; and the use of fluoride containing toothpastes and mouthrinses. Great variations in caries prophylactic effects of aforesaid topical applications have been noted. It has further been indicated from animal experiments that for equal total exposures to fluoride, smaller aliquots applied at higher frequency may be cariostatically more effective than larger aliquots administered at lower frequency. Regolati, Helv. Odont. Acta., Suppl. IX, 1975, pgs. 95–130). Swedish clinical trials have also indicated that frequent rinsing with low fluoride concentrations were more effective in reducing caries increments than rinsing with higher concentrations at longer intervals (P. Torell and Y. Ericsson, *Acta Ondont. Scand.*, 23, 287, 1965).

Consequently, it is desirable to develop a fluorine containing material which is adsorbed onto oral cavity surfaces and has the ability to slowly release fluoride ion, either by physical or chemical means, for relatively long time periods before the agent clears the cavity. The use of such a substantive slow release fluoride agent would provide long term (1–12 hours) availability of low concentration fluoride, and in effect provide a high frequency of application. Such an agent should afford protection for a larger fraction of the day than provided by current fluoride delivery systems.

A series of professionally applied products have been developed such as polyurethane lacquer based on tolylenediisocyante containing 1% of the difluorosilane R-SiF$_2$(OH), fluoride containing silicate cements, fluoride containing acrylic resins, fluoride containing polycarboxylate cement, fluoride containing hydrogel polymers, and the like. However, none of aforesaid products can be used in self-application formulations.

In accordance with this invention, it has now been found that the long chain amine monofluorophosphate is a substantive slow release fluoride agent capable of being used in self-application formulations.

Accordingly, it is an object of this invention to provide a slow release fluoride agent for self-application.

Another object of this invention is to provide an anticaries prophylactic of improved efficiency.

Accordingly, the present invention relates to anticaries oral compositions and to novel bisamine monofluorophosphates represented by the general formula:

(R-NH$_3$)$_2$PO$_3$F, wherein R is a saturated or unsaturated (alkenyl) higher alkyl group containing 8-18 carbon atoms. These compounds have low solubility in water but are dispersible therein particularly in a water-surfactant medium. A 1% aqueous solution or dispersion thereof exhibits a pH of about 5–6. However, in solutions below pH 5 or at high pH (such as above pH 10) it has poorer stability because it hydrolyzes in strong acids or bases. These amine monofluorophosphates exhibit excellent substantivity to simulated oral tissues and tooth enamel, release the fluoride ion slowly within the oral cavity, and inhibit smooth surface and fissure caries. When the alkyl group has less than 8 carbons or more than 18 carbons, poor substantivity to oral surfaces would be expected.

The method of preparing the bislong chain amine monofluorophosphates of instant invention generally comprises reacting a C$_{8-C18}$ amine with monofluorophosphoric acid in a non-aqueous medium at low temperatures, e.g., about 0° C, in accordance with the following reaction, wherein R has the same meaning as above:

$$2RNH_2 + H_2PO_3F \rightarrow (RNH^+_3)_2PO_3F^=.$$

More specifically the bisamine monofluorophosphates are generated by the slow addition of monofluorophosphoric acid to dilute solutions of the long chain amine in an organic solvent while rapidly agitating for about 20 minutes to 2 hours and simultaneously cooling, since the reaction is highly exothermic. Any solvent in which the amine is soluble may be used, such as ethanol, toluene, methanol, propanol, butanol and the like. The period of agitation should be of sufficient duration to effect optimal reaction of the long chain amine. The molar ratio of reactants may be from about 1.4–2 RNH$_2$ to 1H$_2$PO$_3$F to ensure optimal reaction of the amine with the acid. It is preferable that an excess of acid be ulitized. The resultant insoluble solid or waxy reaction product is recovered from a slurry of the organic solvent by filtration or other suitable separation means and is subsequently washed with the solvent and dried under vacuum or air dried for a period of 12 hours to 2 days to essentially completely remove the organic solvent. The drying temperature may be at room temperature and should not exceed about 45° C, i.e. 27°–45° C.

The following examples illustrate the manner in which the compounds of this invention are prepared.

EXAMPLE 1

Preparation of bisoleylamine monofluorophosphate.

14 gms (0.14 mole) of monofluorophosphoric acid is slowly added to 58.66 gm (0.22 moles) of oleylamine in 300 ml toluene immersed in an ice bath to maintain the temperature at about 0° C since the reaction in exothermic, while continuously stirring for about 20 minutes to 2 hours. A solid reaction product settles out of solution and is filtered, and washed while on the filter with aliquot portions of the toluene solvent. The solid reaction product is removed from the filter and is vacuum dried at a temperature of 27°–45° C for 12 hours to 2 days to remove the toluene solvent. Transmission infrared spectra of the oleylamine monofluorophosphate exhibit peaks at 720 cm$^{-1}$ and 790 cm$^{-1}$ indicative of the absorptions of the PO$_3$F$^=$structure; peaks from 1300–1700 cm$^{-1}$ and 2300–3000 cm$^{-1}$ which are typical of RNH$_3^+$ absorptions; and the P-O peak (1110 cm$^{-1}$) is located at an energy intermediate between that of hydroxyapatite (1070 cm$^{-1}$) and Na$_2$PO$_3$F (1175 cm$^{-1}$).

EXAMPLE 2

The procedure of Example 1 is repeated but dodecylamine is substituted for oleylamine. The resulting bisdodecylamine monofluorophosphate exhibits similar infrared spectra as the bisoleylamine monofluorophosphate.

EXAMPLE 3

The procedure of Example 1 is repeated but tetradecylamine is substituted for oleylamine and ethanol was substituted for the toluene. The resulting bistetradecylamine monofluorophosphate exhibits similar infrared spectra as the bisoleylamine monofluorophosphate, which is typical of the bislong chain amine monofluorophosphate.

EXAMPLE 4

Example 3 is repeated, but hexadecylamine is substituted for the tetradecylamine. The resulting bishexadecylamine monofluorophosphate exhibits similar infrared spectra, typical of the bislong chain amine monofluorophosphate.

The process described in Example 1, may be varied by using other suitable non-aqueous solvents such as butanol, ethoxyethanol, propanol, methanol or other organic media in which the long chain amine is soluble; and the ratio of amine to monofluorophosphoric acid may be varied within the range of 1.4 to 2 moles amine per mole of the acid. Other bislong chain amine monofluorophosphates may be prepared by using different long chain amines such as decylamine, nonylamine, octylamine, undecylamine, tridecylamine, and pentadecylamine.

The compounds of this invention may be used in dental compositions such as dental creams or tooth powders at concentrations effective to inhibit caries, namely, an amount of amine monofluorophosphate capable of yielding about 100–5000 parts/million total equivalent $F^-$ upon hydrolysis, preferably about 500–2000 parts/million. The pH for optimum slow release of fluoride is about 5–7, although at somewhat lower (e.g., pH 4) and higher (e.g., pH 8.5) pH values, fluoride release is still slower than is characteristic of fast fluoride release materials such as amine hydro-fluorides.

It has been observed that the bislong chain amine monofluorophosphates described by the foregoing formula exhibit both slow fluoride release and substantivity to structural polysaccharide and human enamel, desirable attributes of an efficient anti-caries agent.

The rate of fluoride ion ($F^-$) release from the bislong chain amine monofluorophosphates was evaluated in vitro with a fluoride ion electrode used in conjunction with a single junction reference electrode and monitored on a millivolt meter against standardized solutions derived from 0.1M and 100ppm NaF solutions and recorded. All measurements were made at pH 5.2 in a 50% total ionic strength activity buffer solution at room temperature (28 ± 2° C), using 20 ml solution containing 10 ml distilled, deionized water and 10 ml total ionic strength activity buffer. 50 mg of the test compounds were introduced into these solutions and the $F^-$ release recorded. Those materials which could not be easily transferred due to physical characteristics (wax or viscous liquid) were added on a small square of glassine weighing paper. Since the bisamine monofluorophosphates have little water solubilities and the amine hydrofluorides are slowly soluble in water, the test compounds were in the form of 0.25% slurries. Sodium monofluorophosphate solid was added as a fluoride release control and its hydrolysis monitored. Although the particle size of the solids did have a slight effect on the initial rate of $F^-$ release, this represented only a minor effect on the overall release rate.

The amine hydrofluorides used for comparison purposes herein were synthesized in non-aqueous solvents by the reaction of concentrated hydrofluoric acid (48%) with the appropriate amine. Compounds prepared were oleyamine·HF, hexadecylamine·HF, etc.

The relative rates of $F^-$ release for potassium dodecylmonofluorophosphate, ethanolamine monofluorophosphate, picolinic acid monofluorophosphate and 2-amino-2-methyl-1,3 propanediol monofluorophosphate indicate that their mode of $F^-$ release is substantially different from that of the bisamine monofluorophosphates of this invention. Instant novel compounds release the fluoride ion at a rate which is typical of monofluorophosphate, namely, slowly; whereas the other amine monofluorophosphates and potassium dodecyl monofluorophosphate

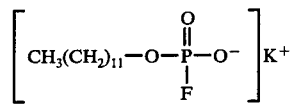

release substantially all the $F^-$ very fast, similarly to the amine hydrofluorides. This almost spontaneous release response is similar to that of a small sample of $NH_4F$. Another interesting observation is that the bislong chain amine monofluorophosphates of this invention have released only a small fraction of their available fluoride in the time period (30 minutes) of this experiment. The results of these tests are summarized in Table 1.

The substantivity of instant bisamine monofluorophosphates to structural polysaccharide substrate was determined by using a Bromophenol blue dye disclosing solution on cotton fabric simulating the soft tissue and plaque in the oral environment. One inch squares of 400-W cotton cloth were agitated in 20 ml slurries containing 1% of the testing agent for 60 seconds; the cloth squares were rinsed under running tap water for 30 seconds, the treated squares were then agitated in 20 ml of 0.05% Bromophenol Blue solution and rinsed for 30 seconds under running water. The squares were dried. The color intensity of the cloth squares is indicative of the degree of substantivity, a strong cloth coloration indicating high substantivity.

As shown in the following Table 1 the bislong chain amine monofluorophosphates exhibit a considerably slower release rate of the fluoride ion and a greater degree of substantivity than other amine monofluorophosphates, potassium dodecylmonofluorophosphate or amine hydrofluorides, resulting in a superior anticaries agent. HF in the following table denotes hydrofluoride, $PO_3F$ denotes monofluorophosphate and AMPD denotes 2-amino-2-methyl-1,3-propanediol.

TABLE 1

| Compound | in vitro F release | Bromophenol Blue reaction | Bromophenol Blue cloth substantivity | State |
|---|---|---|---|---|
| Sodium $PO_3F$ | slow | — | indeterminate | solid |
| bisoleylamine-$PO_3F$ | slow | + | high | waxy solid |

TABLE 1-continued

| Compound | in vitro F release | Bromophenol Blue reaction | Bromophenol Blue cloth substantivity | State |
|---|---|---|---|---|
| picolinic acid-PO₃F | very fast | color change | color change | solid |
| ethanolamine-PO₃F | very fast | — | indeterminate | viscous liq. |
| AMPD-PO₃F | fast | — | indeterminate | waxy solid |
| K⁺[dodecyl PO₃F] | very fast | color change | color change | solid |
| bisdodecylamine-PO₃F | slow | + | very high | solid |
| bistetradecylamine-PO₃F | slow | + | moderate | solid |
| bishexadecylamine-PO₃F | slow | + | moderate | solid |
| bisoctadecylamine-PO₃F | slow | + | ion | solid |
| hexadecylamine-HF | very fast | + | very low | solid |
| oleylamine-HF | very fast | + | very low | solid |

The short chain amine-PO₃F does not react with the Bromophenol Blue, thereby giving an indeterminate result as to degree of substantivity. The acidity of the picolinic acid-PO₃F and K⁺[dodecyl PO₃F] effected a blue→yellow color change on the Bromophenol Blue.

The substantivities of the present bisamine-PO₃F compounds to whole human teeth were evaluated by the Bromophenol Blue disclosing reaction similarly to the cloth test above. In lieu of cloth, precleaned teeth were soaked in human saliva and then treated with a 1% slurry of the test material by shaking vigorously for 60 seconds, followed by a 30 second tap water rinse. The treated teeth were then suspended in 10 ml of a 0.05% Bromophenol Blue solution, agitated and subjected to a 30 second tap water rinse. The extent of adsorption is similar to the cloth tests with the bisoleylamine-PO₃F and the bisdodecylamine-PO₃F exhibiting the highest substantitivities to teeth. The uptake of test materials is much higher in surface cracks and fissures than on smooth surfaces, as evidenced by similar tests run on teeth etched with 0.05 M HClO₄ for 15 seconds. The etched teeth exhibited increased adsorption of the bisamine-PO₃F compounds.

Attenuated total reflectance infrared spectroscopy which is used to evaluate the effects of infrared active chemical agents which interact with the enamel surface shows clearly that once the bisamine monofluorophosphate is adsorbed to the enamel surface in a thin film, it is not easily removed by water rinsing.

The PO₃F⁼ anion, the fluoride releasing active component of the bisamine-PO₃F, is also substantive to the oral and enamel surfaces and to about the same degree as the RNH⁺₃ cation. The Bromophenol Blue dye disclosing reaction determines substantivity of the RNH⁺₃ cation. Transmission IR spectra of films of 0.001 inch thickness of these materials coated on thin polyethylene sheets, before and after rinsing indicates that the absorption bands of the RNH⁺₃ and PO₃F⁼ species decrease only sightly under rinsing but the ratio of the bands I(1625cm⁻¹ for RNH⁺₃)/I(1100cm⁻¹ for PO₃F⁼) does not substantially change due to rinsing. Thus, it can be concluded that both the RNH⁺₃ cation and the PO₃F⁼ anion are substantive to the same degree to substrates found in the oral cavity so that moderate water rinsing alone will not remove a significant amount of the bisamine monofluorophosphate.

When used as a substantive, slow release fluoride, anticaries agent, compounds of the instant invention may be applied directly to the surface to be protected or may be dispersed in a pharmaceutical carrier. Typically, an effective amount (about 100–5000 ppm total F, which may correspond to about e.g., 0.025 to about 10% by weight of the compound) is included in an inert carrier and a dispersing or surface-active agent. Alternatively, the effective amount may be incorporated into a solid carrier which may be inert, such as talc, clay, diatomaceous earth, flour, etc.

When compounds of the instant invention are intended for use in compositions as an anticaries agent, they are typically incorporated in oral or dental preparations in effective amounts typically to provide about 100–5000 ppm total F, preferably about 500–2000 ppm and most preferably about 1000 ppm. For instance, bisoleylamine monofluorophosphate can be preferably employed in amount of about 3.34% by weight, which provides about 1000 ppm total F. Typically, the oral preparation is a dentifrice, such as dental cream, tablet or powder, containing as a vehicle about 20–95% by weight of a water-insoluble polishing material, preferably including water-insoluble phosphate such as insoluble sodium metaphosphate, dicalcium phosphate, tricalcium phosphate, trimagnesium phosphate. The dentifrice may also include water; humectants such as glycerine, sorbitol, propylene glycol 400; detergents; gelling agents such as Irish moss and sodium carboxymethyl cellulose; antibacterial agents; coloring or whitening agents; preservatives; silicones; chlorophyll compounds, additional ammoniated materials; and flavoring or sweetening materials.

The oral composition may also contain detergent surfactants or surface-active agents, e.g., to achieve increased prophylactic action, assist in achieving thorough and complete dispersion of the instant compositions throughout the oral cavity, and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. In addition, the anionics, most commonly used in dentifrices are highly compatible with the compounds of this invention, thereby providing for a stable, homogeneous composition of enhanced anticaries activity. Suitable types of anionic detergents are water-soluble salts of higher fatty acid monoglyceride monosulfates, such as sodium salt of the monosulfated monoglyceride or hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2 hydroxy propane sulfonates, and the substantially saturated higher aliphatic acyl amides of lower aliphatic amino carboxylic acid compounds, such as those having 12 to 16 carbons in the fatty acid alkyl or acyl radicals, and the like. Examples of the last-mentioned amides are N-lauroyl sarcosine, and the sodium, potassium, and ethanolamine salts of N-lauroyl, N-myristoyl or N-palmitoyl sarcosinates, which should be substantially free from soap or similar higher fatty acid material which tends to substantially reduce the effect of these compounds.

The nonionic organic surface active compounds which are contemplated are commercially known and comprise the water-soluble products which are derived from the condensation of an alkylene oxide or equivalent reactant and a reactive-hydrogen hydrophobe. The hydrophobic organic compounds may be aliphatic, aromatic or heterocyclic, although the first two classes are preferred. The preferred types of hydrophobes are higher aliphatic alcohols and alkyl phenols, although others may be used such as carboxylic acids, carboxamides, mercaptans, sulphonamides, etc.. The ethylene oxide condensates with higher alkyl phenols represent a preferred class of nonionic compounds. Usually the hydrophobic moiety should contain at least about 6 carbon atoms, and preferably at least about 8 carbon atoms, and may contain as many as about 50 carbon atoms or more. The amount of alkylene oxide will vary considerably depending upon the hydrophobe, but as a general guide and rule, at least about 5 moles of alkylene oxide per mole of hydrophobe should be used. The upper limit of alkylene oxide will vary also, but no particular criticality can be ascribed thereto. As much as 200 or more moles of alkylene oxide per mole of hydrophobe may be employed. While ethylene oxide is the preferred and predominating oxyalkylating reagent, other lower alkylene oxides such as propylene oxide, butylene oxide, and the like may also be used or substituted in part for the ethylene oxide. Other nonionic compounds which are suitable are the polyoxyalkylene esters of the organic acids such as the higher fatty acids, the rosin acids, tall oil acids, acids from petroleum oxidation products, etc.. These esters will usually contain from about 10 to about 22 carbon atoms in the acid moiety and from about 12 to about 30 moles of ethylene oxide or its equivalent.

Still other nonionic surfactants are the alkylene oxide condensates with the higher fatty acid amides. The fatty acid group will generally contain from about 8 to about 22 carbon atoms and this will be condensed with about 10 to about 50 moles of ethylene oxide as the preferred illustration. The corresponding carboxamides and sulphonamides may also be used as substantial equivalents.

Still another class of nonionic products are the oxyalkylated higher aliphatic alcohols. The fatty alcohols should contain at least 6 carbon atoms, and preferably at least 8 carbon atoms. The most preferred alcohols are lauryl, myristyl, cetyl, stearyl and oleyl alcohols and the said alcohols should be condensed with at least about 6 moles of ethylene oxide, and preferably about 10 to 30 moles of ethylene oxide. A typical nonionic product is oleyl alcohol condensed with 15 moles of ethylene oxide. The corresponding alkyl mercaptans when condensed with ethylene oxide are also suitable in the compositions of the present invention.

Other suitable surface active materials include ampholytic agents such as quaternized imidazole derivatives, which are available under the trademark "Miranol", and cationic surface active germicides and antibacterial compounds such as di-isobutylphenoxyethyl-dimethyl benzyl ammonium chloride, benzyl dimethyl stearyl ammonium chloride, tertiary amines having one fatty alkyl group (of from 12 to 18 carbon atoms) and two polyoxyethylene groups attached to the nitrogen (typically containing a total of from about 2 to 50 ethenoxy groups per molecule) and salts thereof with acids, and compounds of the structure:

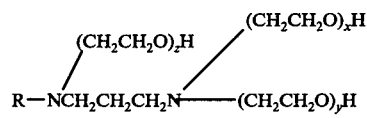

wherein R is a fatty alkyl group containing from about 12 to 18 carbon atoms, and $x$, $y$ and $z$ total 3 or higher, as well as salts thereof with mineral organic acids, may also be used. It is preferred that the total amount of surface-active agent be about 0.05–5% by weight, preferably about 1–3%, of the dentifrice.

The oral preparations are typically applied by brushing the teeth for 30–90 seconds at least once daily. Typical oral preparations of the invention which can be applied in this manner are set forth below.

EXAMPLE 5

| Dental Cream | % |
|---|---|
| bis Oleylamine monofluorophosphate | 0.77 |
| Sodium lauryl sulfate | 1.00 |
| Glycerine | 22.00 |
| Sodium pyrophosphate | 0.25 |
| Carboxymethyl cellulose | 0.85 |
| Sodium saccharin | 0.20 |
| Sodium benzoate | 0.50 |
| Calcium carbonate (precipitated) | 5.00 |
| Dicalcium phosphate dihydrate | 46.85 |
| Flavor | 0.80 |
| Water | Q.S. to 100 |

The bisoleylamine monofluorophosphate is roller milled into the dental cream formed by thoroughly mixing the rest of the ingredients. The final dental cream formed is loaded into tubes and stored at room temperature. The pH of 20% slurry is about 6.5. This produce exhibits a long shelf-life, i.e., is stable with respect to $F^-$ released by hydrolysis of the active material.

EXAMPLE 6

0.78% bisdodecylamine monofluorophosphate is used in lieu of the bisamine fluorophosphate in Example 5. A homogeneous, stable dentifrice effective in inhibiting smooth surface and fissure caries is obtained.

EXAMPLE 7

0.76% bistetradecylamine monofluorophosphate is used in lieu of the amine monofluorophosphate of Example 5.

EXAMPLE 8

1.00% of bishexadecylamine monofluorophosphate is used in lieu of the bisamine monofluorophosphate of Example 5.

EXAMPLE 9

0.5% bisoctadecylamine monofluorophosphate is used in lieu of the bisamine monofluorophosphate of Example 5.

EXAMPLE 10

0.77% bisdecylamine monofluorophosphate is used in lieu of the bisamine monofluorophosphate of Example 5.

The oral composition inhibits caries and are effective against dentinal fissure lesions as well as smooth surface lesions.

Although this invention has been described with reference to specific examples, it will be apparent to one skilled in the art that various modifications may be made thereto which fall within its scope.

We claim:

1. A bislong chain amine monofluorophosphate which is a substantive, slow release fluoride agent and which has the structural formula:

(RNH₃)₂PO₃F wherein R is a unsaturated saturated alkyl or unsaturated alkenyl group containing 8-18 carbon atoms.

2. A compound in accordance with claim 1 having the formula of bisoleylamine monofluorophosphate.

3. A compound in accordance with claim 1 having the formula of bisdodecylamine monofluorophosphate.

4. An anticaries pharmaceutically acceptable oral composition containing an effective amount of the substantive, slow release fluoride agent defined in claim 1 admixed with a pharmaceutical carrier.

5. An anticaries pharmaceutically acceptable oral composition containing an effective amount of the substantive, slow release fluoride agent defined in claim 1 admixed with an oral preparation.

6. An anticaries pharmaceutically acceptable oral composition in accordance with claim 5 wherein said substantive, slow release fluoride agent is present in amount which yields about 100-5000 parts per million total equivalent fluoride.

7. An anticaries pharmaceutically acceptable oral composition in accordance with claim 6 wherein said amount is about 500-2000 parts per million total equivalent fluoride.

8. An anticaries pharmaceutically acceptable oral composition in accordance with claim 5 wherein the pH of said composition is about 5-7.

9. An anticaries pharmaceutically acceptable oral composition in accordance with claim 6 wherein said substantive, slow release agent is oleylamine monofluorophosphate.

Disclaimer

4,105,759.—*Ronald Stanley Schreiber*, Highland Park, N.J. and *Edward John Duff*, Sandbach, England. AMINE MONOFLUOROPHOSPHATES IN DENTIFRICES. Patent dated Aug. 8, 1978. Disclaimer filed Jan. 29, 1981, by the assignee, *Colgate-Palmolive Co.*

Hereby enters this disclaimer to claims 1-4 of said patent.
[*Official Gazette April 14, 1981.*]